United States Patent [19]

Urso

[11] Patent Number: 4,774,931
[45] Date of Patent: * Oct. 4, 1988

[54] SAFETY HEATER

[76] Inventor: Charles L. Urso, 215 Newton St., Waltham, Mass. 02154

[*] Notice: The portion of the term of this patent subsequent to Sep. 2, 2004 has been disclaimed.

[21] Appl. No.: 46,670

[22] Filed: May 4, 1987

Related U.S. Application Data

[63] Continuation-in-part of Ser. No. 919,086, Oct. 14, 1986, Pat. No. 4,691,688, which is a continuation-in-part of Ser. No. 717,310, Mar. 29, 1985, abandoned, which is a continuation-in-part of Ser. No. 644,987, Aug. 28, 1984, abandoned, which is a continuation-in-part of Ser. No. 642,059, Aug. 20, 1984, abandoned.

[51] Int. Cl.[4] .......................... F23L 17/04; F24C 5/16
[52] U.S. Cl. .................................. 126/85 B; 126/59; 126/93; 126/94; 126/307 R; 126/314; 431/88
[58] Field of Search ...................... 126/59, 59.5, 85 B, 126/93, 95, 94, 204, 208, 262, 265, 266, 307 R, 314; 431/88, 200, 201, 343, 344, 354

[56] References Cited

U.S. PATENT DOCUMENTS

| | | | |
|---|---|---|---|
| 324,715 | 8/1885 | Matthews | 431/88 |
| 877,349 | 1/1908 | Little | 126/65 |
| 1,023,055 | 4/1912 | Wilson | 126/52.5 |
| 1,064,610 | 6/1913 | Canfield | 126/314 |
| 2,567,323 | 9/1951 | Cyphert | 126/96 |
| 2,843,105 | 7/1958 | Badish | 126/58 |
| 2,845,924 | 8/1958 | Benda | 126/208 |
| 2,904,031 | 9/1959 | Scott | 126/204 |
| 2,941,525 | 6/1960 | Harshfield | 126/85 B |
| 2,966,838 | 1/1961 | Thompson et al. | 126/85 B |
| 3,192,852 | 7/1965 | Stark et al. | 126/85 B |
| 3,274,989 | 9/1966 | Jenson et al. | 126/85 B X |
| 3,693,610 | 9/1972 | Erlichmann | 126/85 B |
| 4,351,314 | 9/1982 | Morton | 126/59 |
| 4,475,532 | 10/1984 | Woods | 126/204 |
| 4,691,688 | 9/1987 | Urso | 126/208 |

FOREIGN PATENT DOCUMENTS 354153  8/1931  United Kingdom .............. 126/85 B Primary Examiner—Samuel Scott
Assistant Examiner—Allen J. Flanigan
Attorney, Agent, or Firm—Hamilton, Brooks, Smith & Reynolds

[57] ABSTRACT

A portable heater comprising a double-wall vessel which forms a combustion chamber and encloses a suitable fuel. Air passages provide an airflow through the vessel for supporting combustion. Also included are endless conduits which entrap displaced fuel to prevent it from escaping from the heater through the air passages. Thus, fuel is prevented from escaping from the heater in all positions of the same in the event that the heater is dropped or otherwise upset. A set of cooling fins, encircling a fuel holder, cool the fuel to help maintain an even burn rate. The heater further includes an adjustable flame attenuator for selective heat control. At a low heat setting the invention may be used as a personal or close contact heater wherein an outer wall serves as a guard for preventing contact burns. A modified embodiment of the heater, for use in a tent, includes an air intake tube and a fuel for exchanging gases with the outside of the tent.

6 Claims, 3 Drawing Sheets

SAFETY HEATER

RELATED APPLICATIONS

This is a continuation-in-part of application Ser. No. 919,086 filed Oct. 14, 1986 now U.S. Pat. No. 4,691,688 which is a continuation-in-part of Ser. No. 717,310 filed Mar. 29, 1985 (now abandoned) which is a continuation-in-part of Ser. No. 644,987 filed Aug. 28, 1984 (now abandoned) and of Ser. No. 642,059 filed Aug. 20, 1984 (now abandoned).

TECHNICAL FIELD

This invention relates to portable heaters and specifically to portable heaters which utilize combustible fuels.

BACKGROUND OF THE INVENTION

Portable heaters utilizing combustible materials as fuel have long been known in the art. Need for these devices often arises in locations where household electric power is unavailable. Typical conditions or locations where such devices are needed, therefore, include football games, parked vehicles, ice fishing sites, campsites, tents, remote cabins, power failure emergencies, and outdoor spectator events. Widespread use of such portable heaters, however, has been restricted by potential hazards which stem from the use of combustible materials. Problems which have been encountered include fires, chemical burns, and thermal burns. Many of these accidents have occurred as result of dropping or knocking the heaters over wherein there is spillage or escape of fuel. Further, such devices are generally unsuitable for use in the presents of children unless they are constantly monitored. The necessity of constantly monitoring such devices further restricts their use. It is an object of this invention, therefore, to provide an improved portable heater which includes safety features for the preparation of accidental fire or burns.

SUMMARY OF THE INVENTION

The present invention comprises a double-wall vessel or enclosure which forms a combustion chamber and encloses a suitable fuel. Air passages provide an airflow through the enclosure for supporting combustion. Also included are endless conduits which entrap displaced fuel to prevent it from escaping from the heater through the air passages. Thus, fuel is prevented from escaping from the heater in all positions of the same in the event that the heater is dropped or otherwise upset.

The heater includes a set of cooling fins, encircling a fuel holder, for cooling the fuel to help maintain an even burn rate. The heater further includes an adjustable flame attenuator for selective heat control. At a low heat setting the invention may be used as a personal or close contact heater wherein an outer wall serves as a guard for preventing contact burns.

A modified embodiment of the heater, for use in a tent, includes an intake tube and a flue for exchanging gases with the outside of the tent.

BRIEF DESCRIPTION OF THE DRAWINGS

The accompanying drawings, in combination with the description herein, illustrate features and advantages of the invention. Like reference characters in different views refer to the same parts. The drawings are intended to illustrate principles of the invention and are not necessarily to scale and in which drawings.

DETAILED DESCRIPTION OF THE INVENTION

Figure 1:
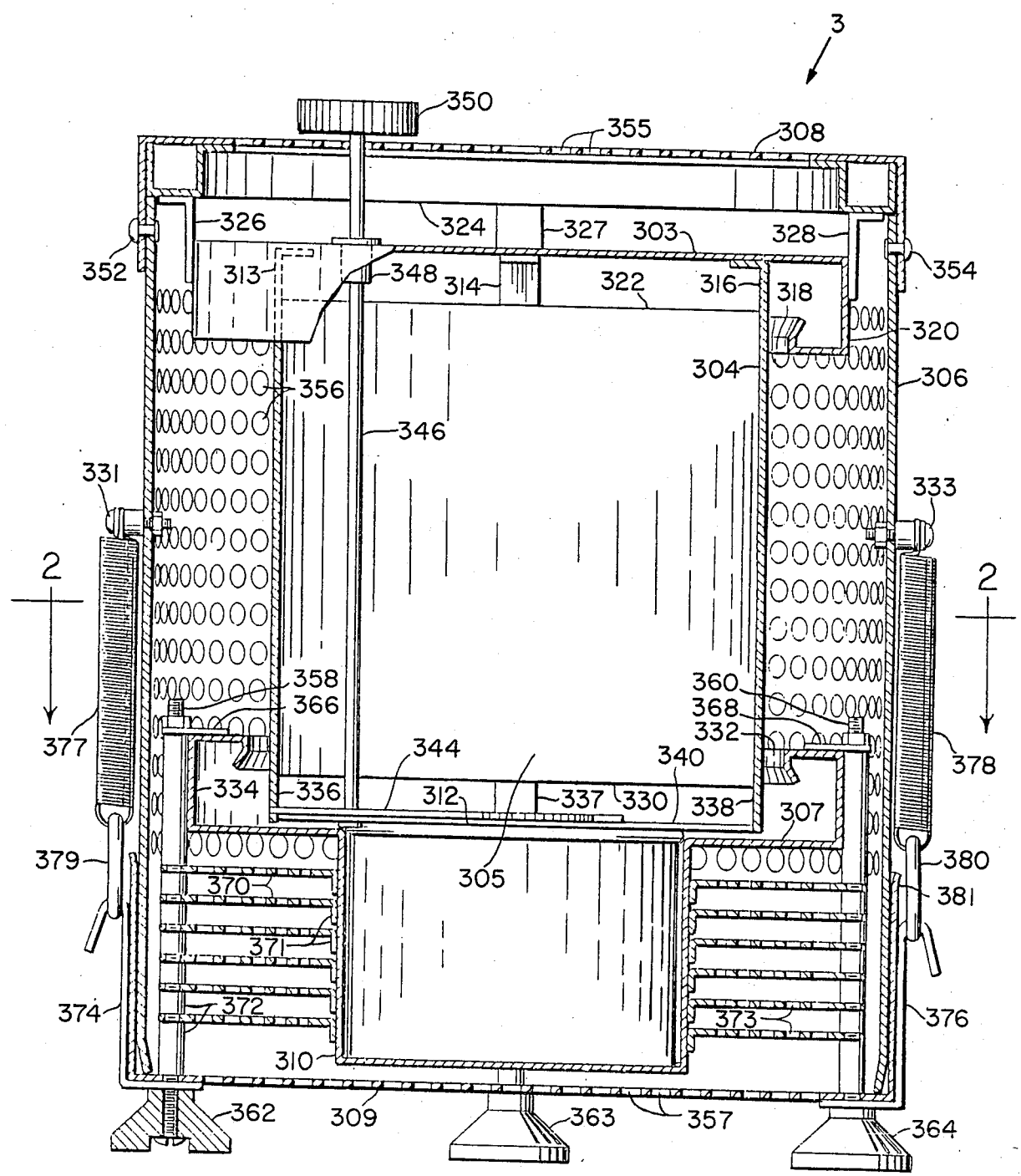
FIG. 1 is a cross-sectional view of the invention taken along its longitudinal centerline.

A portable safety heater embodying the principles of this invention is shown in cross-section in FIGS. 1 and is identified generally by the numeral 3. The heater 3 comprises an inner enclosure including an inner cylinder, or inner container, 304 which forms a combustion chamber 305. Inner cylinder 304 is capped at both ends by inner caps 303, 307 and is surrounded by an outer enclosure including an outer cylinder, or outer container, 306. Outer cylinder 306 is capped by outer caps 308, 309.

A central portion of the lower inner cap 307 is formed into a cup-shaped well or holder 310 which receives a closely fitted fuel can 312. The fuel can contains jelled fuel of the type commonly used for heating portable stoves and chafing dishes. Holder 310 extends downwardly away from the combustion chamber 305.

The inner cylinder is an open-ended tube that has a plurality of evenly spaced tines 313, 314, 316 (a similar fourth tine is sectioned away and is therefore not shown) extending upwardly and inwardly at its upper end. The tines provide a mounting surface for the top inner cap 303. The cap is permanently attached to the tines by welding or fasteners.

The top inner cap 303 has an annular mouth 318 larger than the outer diameter of the inner cylinder 304. A peripheral portion of the cap 303 is formed into a continuous open conduit 320 that surrounds an upper end portion of the inner cylinder. The conduit opening is positioned around the upper end 322 of the inner cylinder. Thus, conduit 320 entraps loosened fuel or debris from the combustion chamber 305 or the fuel can 312 if the heater is upset. An air passage, between the inner cylinder 304 and conduit 320, permits the passage of gases between the interior and the exterior of the combustion chamber.

Top inner cap 303 is permanently attached to top outer cap 308 by means of a mounting ring 324 having a U-shaped cross-section. A leg of the ring's "U" is spot welded or riveted to the inner surface of cap 308. A plurality of evenly spaced L-shaped brackets 326, 327, 328 (a similar fourth bracket is sectioned away and is therefore not shown) each have a leg welded to inner cap 303. An opposite leg of each bracket is welded or riveted to ring 324. Thus, cap 303 is fixed in spaced relation to cap 308 thereby reducing conductive transfer of heat from the former to the latter.

A lower end portion of the inner cylinder 304 extends coaxially into the lower inner cap 307. The inner cylinder's lower end 330 is positioned above the inner surface of lower cap 307. Cap 307 is similar to cap 303 and has an annular mouth 332 larger than the outer diameter of the inner cylinder 304. A peripheral portion of the cap 307 is formed into a continuous open conduit 334 that surrounds the lower end portion of the inner cylinder. The conduit opening surrounds the lower end 330 of the inner cylinder. Thus, conduit 334 entraps loosened fuel or debris from the combustion chamber 305 or the fuel can 312 if the heater is upset. An air passage, between the inner cylinder 304 and conduit 334, permits the passage of gases between the interior and the exterior of the combustion chamber.

In concert, the upper and lower air passages produce an airflow sufficient to support efficient combustion of the fuel in can 312. The conduits are positioned to act as safety devices which, while permitting airflow, bar the escape of fuel or debris into the environment where they might be hazardous.

Extending downwardly from the lower end of the inner cylinder 304 is a plurality of evenly spaced tines 336, 337, 338 (a similar fourth tine is sectioned away and is therefore not shown). Lower end portions of the tines are received in notches (not shown) in the periphery of a circular plate 340 (FIGS. 1 and 2) where the tines are welded to the plate. Plate 340 has a central aperture 342 (FIG. 2) coaxially positioned at the mouth of the fuel can 312. An inner peripheral portion of plate 340, which surrounds aperture 342, is in contact with the top of the fuel can. Thus, gases entering or leaving the interior of the fuel can must pass through aperture 342.

Figure 2:
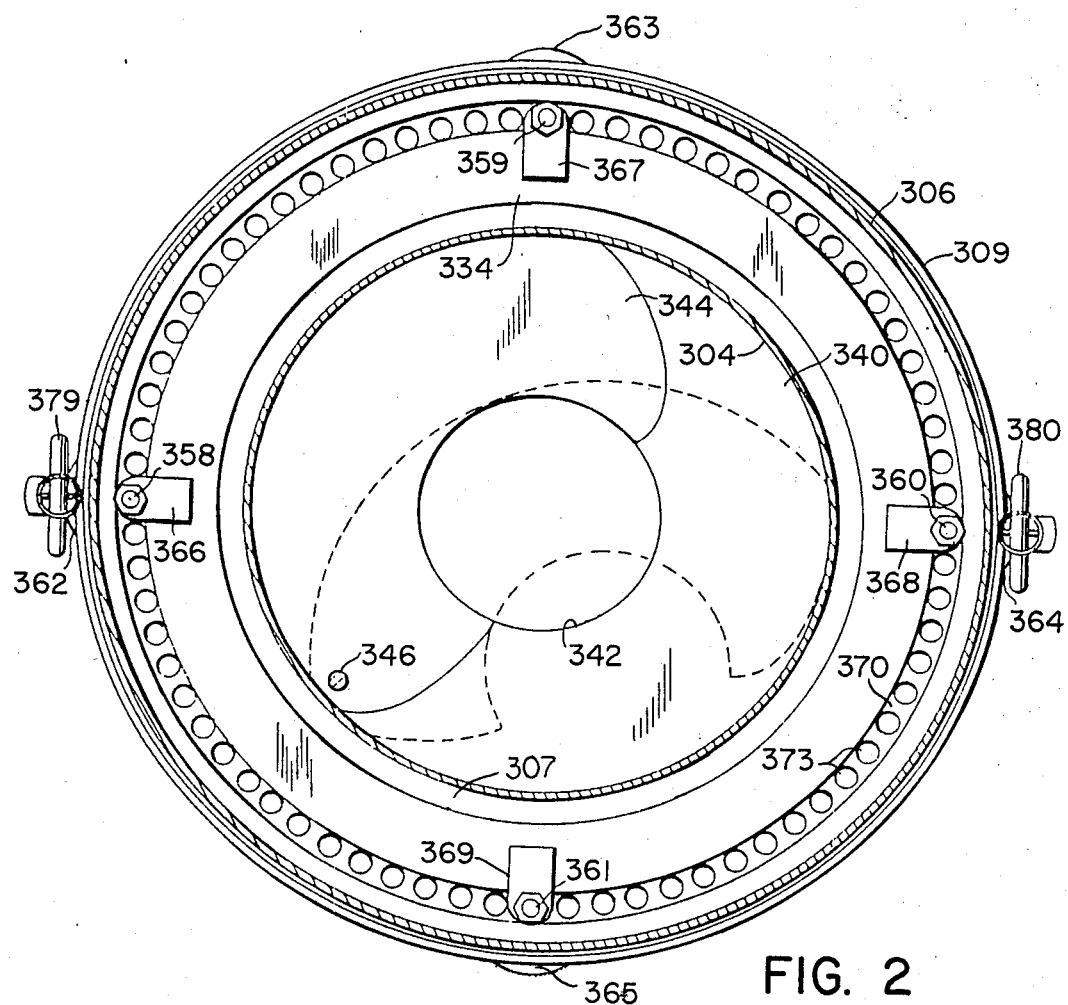
FIG. 2 is cross-sectional view of the invention of FIG. 1 taken along the line 2—2 of FIG. 1.

Pivotally mounted on top of plate 340 is a flame attenuator 344 (FIGS. 1 and 2). The attenuator 344 is fixed to a shaft 346 which has a lower end portion journaled in a small hole drilled through plate 340. The lower end of shaft 346 is flared to prevent the shaft from coming out of the hole. Attenuator 344 can be pivoted, by means of the shaft, between open and closed positions. The attenuator is shaped such that in the open position (shown in FIG. 2) a maximum amount of gases can pass through aperture 342. In the close position (dashed line in FIG. 2) the attenuator blocks most of aperture 342 to minimize gaseous passage.

An upper portion of the shaft 346 is journaled in a bearing 348 welded to cap 303. The bearing 348 and shaft 346 pass through an aperture in cap 303 so that an upper end portion of the shaft can further extend through an aperture in outer cap 308. A knob 350, fixedly attached to the top end of the shaft, provides a means to pivot the shaft and the flame attenuator. Thus, knob 350 can be used to selectively control the heat output of the safety heater.

Outer cylinder 306, which is coaxial with the inner cylinder 304, is permanently capped at its upper end by cap 308. Rivets 352, 354 hold the cap 308 and cylinder 306 together. Both outer caps 308, 309 and outer cylinder 306 are perforated with perforations 355, 356, 357. Cylinder 306 can be formed from perforated flat stock, such as flattened expanded metal, which can be rolled and the seam can be butt welded. A lower end portion of cylinder 306 is received within the lower outer cap 309 and rests on the bottom inner surface of the same.

Lower inner cap 307 is permanently attached, in spaced relation, to lower outer cap 309 by bolts 358, 359, 360, 361 (FIGS. 1 and 2). Sleeve spacers 372, which encircle each bolt, space the caps 307, 309 apart. Each bolt passes through a respective support leg 362, 363, 364, 365, cap 309, and its respective spacers 372. Anchoring each bolt to cap 307 is achieved by passing it through a respective lug 366, 367, 368, 369 welded to the cap.

Encircling the fuel can holder 310 are annular cooling fins 370 having collars 371 (FIG. 1) tightly surrounding the holder. The bolts 358, 359, 360, 361 pass through apertures in peripheral portions of the fins wherein the spacers 372 are placed above and below each fin. Thus, the bolts and spacers help support and evenly space the fins. Each fin 370 is pierced with perforations 373.

The purpose of the fins is to draw heat away from the fuel can holder 310 and fuel can 312 to keep the fuel relatively cool. This helps to keep the fuel burning at an even rate by preventing it from vaporizing excessively at the higher heat settings of the attenuator. Warm air rising from the heater draws relatively cool air through perforations 357 and through the perforations 373 of each fin for heat exchange.

An optional modification (not shown) of the fins 370 includes the elimination of perforations 373. Each fin would then have a plurality of equidistant radial cuts extending inwardly from its outer edge to, but not into, its collar 371. This would divide the fin into a set of blades resembling fan blades. Each blade would also be twisted ninety degrees about its radial axis so that the faces of the blade are substantially vertical. Thus, the fins would resemble impellers wherein air rising between the blades would result in heat exchange.

Figure 3:
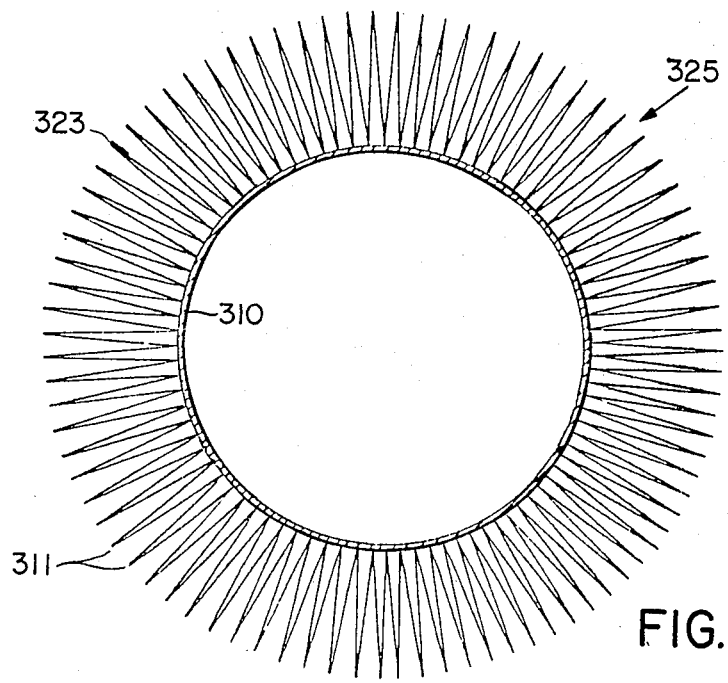
FIG. 3 is a cross-sectional view of another embodiment of the invention taken perpendicularly across its vertical axis and shows a cooling collar encircling the holder.

A simple alternative method of devising cooling fins for fuel holder 310 is shown in FIG. 3. The holder is shown in cross-section surrounded by a cooling collar 325. The collar comprises a plurality of cooling fins 311 which are formed from a single strip of thin metal bent at acute angles in alternating directions. Thus, the largest surfaces of the fins 311 are positioned parallel to the axis of the holder. The two ends of the strip are folded together to form a joint 323. An annular clamp or strap (not shown) can be tightened around the collar 325 to insure firm contact of all the fins with fuel holder 310. A space (not shown) would be left between cap 307 and the top of collar 325 so that air rising between the fins 311 is not trapped under the cap. The vertical height of the fins 311 is substantially equal to the height of holder 310 minus the weight of the space mentioned in the previous sentence.

The cooling fins, whichever are used in the invention, are protected from damage by being permanently enclosed between the lower caps 307, 309.

Safety heater 3 also comprises upper and lower permanent subassemblies. The lower subassembly comprises both lower caps 307, 309, fins 370, legs 362, 363, 364, 365, and their associated fastening means. The upper subassembly comprises both cylinders 304, 306, both upper caps 303, 308, plate 340, flame attenuator 344, shaft 346, knob 350, and their associated fastening means.

Spring latches secure the two subassemblies together. The latches comprise two hooks 374, 376 (FIG. 1) affixed to diametrically opposite locations on lower cap 309 by bolts 358, 360. End portions of two springs 377, 378 are fixed to diametrically opposite locations on the outer cylinder with fasteners 331, 333. An opposite end portion of each spring 377, 378 is attached to a respective ring 379, 380. Thus, the rings can be placed on the hooks under spring tension to secure the subassemblies together. This latch is simple, yet very effective in preventing accidental separation of the subassemblies. The springs may be chosen with sufficient strength to prevent a child from unlatching the heater.

The heater can be disassembled for access to its interior by unhooking the rings 379, 380. Access to the interior of the heater is required for igniting the fuel and replacement of the fuel can 312.

To guide and facilitate its entry into cap 309, the outer cylinder's lower end portion is curved slightly inward while the top edge the rim 381 of cap 309 is curved slightly outward.

Heat output from the heater can be reduced with the control knob 350 to a level such that the outer cylinder and outer caps can serve as a guard to protect the user from burns. In that operational mode, the user can safely come in close contact with the heater. For example, he can place the device between his feet or on his lap while in a sitting position when watching spectator sports; as in a football stadium. Outdoors, in that position, a blanket or poncho partially covering himself and the heater would trap warm air for greater comfort. If the heater were to be used exclusively for this purpose, it can be modified to keep the heat level permanently low by restricting the flame attenuator selections.

Permanent attachment of components, referred to above as being "welded", may alternatively be fixed with fasteners such as rivets. Note that except for the lugs, all the components of the lower subassembly are held together by only four bolts. This, of course, saves assembly time and expense for production of the heater.

MODIFIED EMBODIMENT FOR HEATING TENTS

Figure 4:
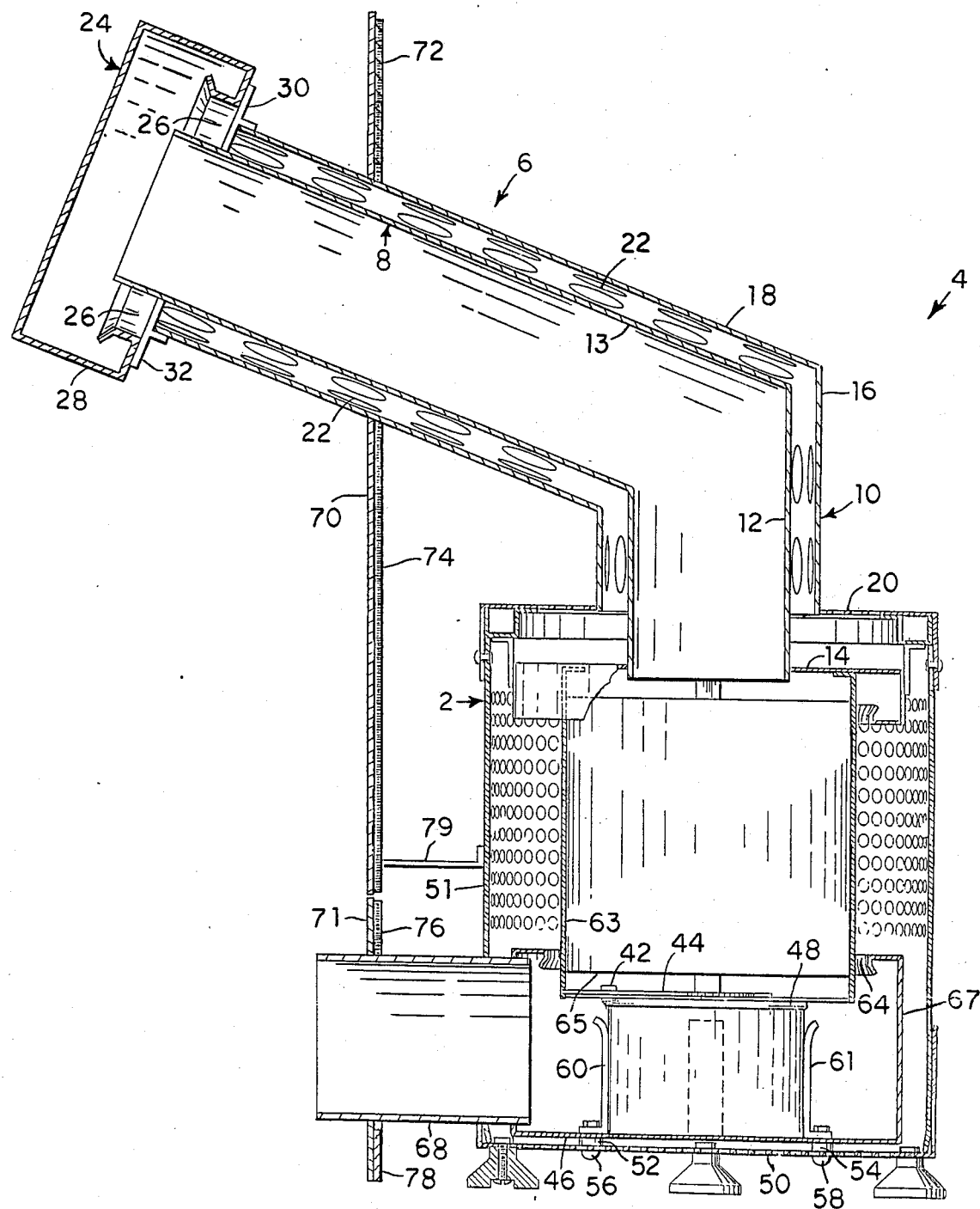
FIG. 4 is a modified embodiment of the invention showing a cross-sectional view taken along its longitudinal centerline.

Shown in FIG. 4, identified generally by the numeral 4, is a modified embodiment of the safety heater. It is designed for use in tents, especially small tents, where it might be desirable to have gaseous communication between the heater and the atmospheric air outside the tent.

The heater 4 includes a double-wall flue 6 comprised of an inner tube 8 surrounded by a outer tube 10 which is spaced from the inner tube. Both tubes have circular cross-sections.

Inner tube 8 includes a vertical portion 12 contiguous with a transverse portion 13. The vertical portion 12 has an end portion tightly fitted in a central aperture in the top inner cap 14 such that the end portion protrudes into the cap beyond the cap wall. Thus, loose fuel in cap 14 is prevented from dripping into the flue if the heater is turned upside-down. Inner tube 8 is welded to the circumferential edge of the cap 14 central aperture to form a liquid tight seal. An upper end of the tube vertical portion 12 is welded to an end of the tube transverse portion 13 to form an angled joint.

Outer tube 10 includes a vertical portion 16 contiguous with a transverse portion 18. The vertical portion 16 has an end portion received in a central aperture in the top outer cap 20. Outer tube 10 is welded to the circumferential edge of the cap 20 central aperture. An upper end of the tube vertical portion 16 is welded to an end of the tube transverse portion 18 to form an angled joint.

The outer tube 10 is liberally perforated with perforations 22. Though the perforations are shown as circular, other shapes can be used. For example, outer tube 10 can be constructed from expanded metal having diamond shaped perforations.

The distal end of the flue 6 is capped by a trap cap 24 constructed similar to the heater inner caps. Cap 24 has an annular mouth 26 larger than the outer diameter of the flue 6. A peripheral portion of cap 24 is formed into a continuous open conduit 28 that surrounds a distal end portion of the flue. The conduit opening is positioned around a distal end portion of the inner tube 8. Thus, conduit 28 entraps fuel or debris from the fuel can 48 in the unlikely event that such material should travel through the flue as result of an upset or disturbance of the heater. The cap 24 also prevents wind driven rain or snow from entering the flue. T-shaped brackets 30, 32 welded to cap 24 and outer tube 10, as shown in the figure, hold the cap, outer tube, and inner tube properly spaced from each other. Combustion gases passing through the flue are expelled out from cap 24 through its annular mouth 26.

A lower portion of the lower inner cap 46 is extended downward to form the shape of a cylindrical pan. The cap 46 is taller and wider than the fuel can 48 which is contained within the cap and rests on the floor of the same. Inner cap 46 is spaced from the lower outer cap 50 by means of spacers 52, 54.

Passing through the spacers 52, 54 are fasteners, such as screws, 56, 58, respectively, which hold L-shaped brackets 60, 61 and caps 46, 50 fixed to each other. Brackets 60, 61, along with two similar brackets (indicated by dashed line) held by similar means (not shown), are positioned around the fuel can 48 to serve as a holder for the can. The fuel can 48 may be lifted out or inserted in the holder as needed.

A lower end portion of the inner cylinder 63 extends coaxially into the lower inner cap 46. The inner cylinder's lower end 65 is positioned above the inner surface of lower cap 46. Cap 46 is similar to cap 307 of heater 3 in that is has an annular mouth 64 larger than the outer diameter of the inner cylinder 63. A peripheral portion of the cap 46 is formed into a continuous open conduit 67 that surrounds the lower end portion of the inner cylinder. The conduit opening surrounds the lower end 65 of the inner cylinder. Thus, conduit 67 entraps loosened fuel or debris from the fuel can 48 if the heater is upset.

Passing through an aperture through a vertical wall of the cap 46 is an air intake tube 68 having a distal end portion and a mesial end portion. The mesial end portion is welded to the periphery of the cap aperture to form a liquid tight seal around the tube 68. The mesial end of the tube projects inwardly beyond the cap wall so that fuel spilled within the cap 46 is prevented from entering the intake tube 68 if the heater is turned such that the intake tube is the lowest part of the heater. However, the distal end portion of intake tube 68 could also be provided with a trap cap similar to cap 24 for even greater safety.

A rectangular upper flange 70, having an elliptical aperture, is vertically positioned so that the flue 6 is fitted through the aperture and tack welded to the flange. The flange 70, being about twice as wide in its horizontal dimension as the diameter of the flue 6, surrounds the flue. A lower end portion of the flange 70 is supported by an L-shaped bracket 79 welded to the flange and to the outer enclosure 2.

A lower rectangular flange 71, having a circular aperture, receives the intake tube 68 within the aperture. The width of the lower flange 71, in its horizontal dimension, is the same as that of the upper flange 70. Lower flange 71 is tack welded to the tube 68 in a position such that the lower flange is aligned and contiguous with the upper flange 70.

In order to accommodate the intake tube 68, the outer cylinder 51 includes a bottomless opening shaped like an upsidedown U (not shown) cut around the intake tube. Thus, the upper subassembly of the heater 4 can be lifted off of the lower subassembly in the same way as described for the heater 3. In heater 4, however, the upper subassembly includes the flue 6 and flange 70 wherein the lower subassembly includes the intake tube 68 and flange 71.

Cemented around outer peripheral portions of the upper and lower flanges 70, 71 are strips of Velcro 72, 74, 76, 78 positioned to form a rectangular Velcro border.

During operation of the heater 4, its main body is positioned inside a tent (not shown) adjacent the tent entry. The transverse portion of the flue 6 and the intake tube 68 pass through a partially open zipper of the tent entry so that the distal end portion of the flue, cap 24, and the distal end of the intake tube are outside of the tent. Strips of Velcro (that can mate or "stick" to the Velcro strips 72, 74, 76, 78) can be attached to the exterior surface of the tent, alongside each half of the zipper. Thus, peripheral portions of the tent entry can be closed around the flue 6 and intake tube 68 and be detachably fixed to the flanges 70, 71 by means of the Velcro. Hence, the flanges block the entry while the Velcro seals the same thereby protecting tent occupants from outside weather.

Outer tube 10 is spaced from inner tube 8 so that free air can flow between the inner and outer tubes and through the perforations 22 during operation of the heater. The airflow keeps the outer tube relatively cool while dissipating thermal energy from the surface of inner tube.

Atmospheric air is drawn from outside the tent through intake tube 68. The entering air cools the fuel can 48, to help maintain an even burn rate, and supports combustion of the fuel. Thus, the tent occupants are not threatened by the oxygen consumption of the heater nor by combustion gases.

The main body of the heater 4 is the same as that of heater 3 except as explained above and except that there is no control knob and no control knob shaft. Replacing the control knob shaft is a rivet 42 so that the flame attenuator 44 can pivot around the rivet. In this case, the flame attenuator must be adjusted before the heater 4 subassemblies are latched together; just before or after igniting the fuel, for example. The subassemblies are latched together by the same means as that of heater 3.

Each of the described heater embodiments is designed to entrap liquid, solid, or semisolid debris within its continuous conduits if the device is dropped or otherwise upset while operating. The debris are then quickly consumed without hazard. For example, if the heater is tipped over, any displaced fuel simply drips into the cap conduits and is trapped. If the safety heater is placed completely upside-down, the displaced fuel will also be safely entrapped in the caps or cap conduits. The entrapment system functions in all positions of the heater.

Other modifications could replace tube 68 with an air intake tube of rectangular cross-section having its widest diameter the size of the diameter of flue 6, for example. It is understood that various modifications can be made of the embodiments illustrated and described herein without departing from the spirit of the invention as expressed in the following claims.

What is claimed is:

1. A portable safety heater comprising:
   a fuel source;
   an enclosure enclosing the fuel source, the enclosure having an air passage for supporting combustion of fuel;
   a flue for conveying combustion gases away from the enclosure, the flue including a tube connected to the enclosure such that the tube is in gaseous communication with the interior of the enclosure; and
   means for entrapping nongaseous fuel passing through the flue in the event that the heater is disturbed.

2. The portable safety heater as defined in claim 1, wherein the fuel entrapping means comprises a trap cap for at least partially enclosing an end portion of at least one of the tubes, the cap having a peripheral portion formed into a fuel entrapping conduit.

3. A portable safety heater comprising:
   a fuel source;
   an enclosure enclosing the fuel source, the enclosure having an air passage for supporting combustion of fuel;
   a flue for conveying combustion gases away from the enclosure, the flue including a tube connected to the enclosure such that the tube is in gaseous communication with the interior of the enclosure;
   an air intake tube for conveying atmospheric air to the interior of the enclosure in order to support combustion of fuel, the intake tube being connected to the enclosure such that the intake tube is in gaseous communication with the interior of the enclosure; and
   means for entrapping nongaseous fuel passing through at least one of the tubes of the flue and intake tube combination in the event that the heater is disturbed.

4. The portable safety heater as defined in claim 3, wherein the fuel entrapping means comprises at least one trap cap for at least partially enclosing an end portion of at least one of the tubes, the cap having a peripheral portion formed into a fuel entrapping conduit.

5. A portable safety heater comprising:
   a fuel source;
   an enclosure having at least one side for enclosing the fuel source said enclosure being supported in an upright position in which said at least one side is upstanding, the enclosure including at least one open conduit having a portion in spaced relation to an enclosure wall such that a gap therebetween provides a passage which leads to the interior of the enclosure for gaseous passage between the interior and exterior of the enclosure for supporting combustion of fuel, wherein the conduit collects fuel displaced from the fuel source thereby preventing the fuel from escaping from the heater if one enclosure is displaced from the upright position to onto its side.

6. A portable safety heater comprising:
   a fuel source;
   a first subassembly having an end portion;
   a second subassembly connected to the first subassembly wherein the combination of subassemblies encloses the fuel source and include at least one air passage for supporting combustion of the fuel, the second subassembly having an open conduit surrounding the end portion of the first subassembly such that the conduit collects fuel displaced from the fuel source thereby preventing the fuel from escaping from the heater

* * * * *

UNITED STATES PATENT AND TRADEMARK OFFICE
CERTIFICATE OF CORRECTION

PATENT NO. : 4,774,931

DATED : October 4, 1988

INVENTOR(S) : Charles L. Urso

It is certified that error appears in the above-identified patent and that said Letters Patent is hereby corrected as shown below:

Title page:

Under References Cited, U.S. PATENT DOCUMENTS, thirteenth reference, change "Erlichmann" to --Ehrlichmann--.

Under ABSTRACT, line 17, change "fuel" to --flue--.

Col. 3, line 38, change "close" to --closed--.

Col. 4, line 42, change "weight" to --height--.

Col. 6, line 32, change "is" to --it--.

Col. 8, line 43, after "source", insert a comma.

Col. 8, line 43, change "supported" to --supportable--.

Col. 8, line 54, change "one" to --the--.

Col. 8, line 55, delete the word "to".

Signed and Sealed this

Fifth Day of September, 1989

*Attest:*

DONALD J. QUIGG

*Attesting Officer*

*Commissioner of Patents and Trademarks*